United States Patent
Lang et al.

(10) Patent No.: US 8,204,572 B1
(45) Date of Patent: Jun. 19, 2012

(54) MEDICAL ELECTRODE

(75) Inventors: Burrhus Lang, Innsbruck (AT); Sergius Lang, Innsbruck (AT)

(73) Assignee: Leonard Lang KG, Innsbruck (AT)

( * ) Notice: Subject to any disclaimer, the term of this patent is extended or adjusted under 35 U.S.C. 154(b) by 0 days.

(21) Appl. No.: 10/030,519

(22) PCT Filed: Apr. 19, 2000

(86) PCT No.: PCT/AT00/00098
§ 371 (c)(1),
(2), (4) Date: Jun. 5, 2002

(87) PCT Pub. No.: WO00/65993
PCT Pub. Date: Nov. 9, 2000

(30) Foreign Application Priority Data

Apr. 29, 1999 (AT) .......................................... 769/99

(51) Int. Cl.
*A61B 5/04* (2006.01)
*A61N 1/00* (2006.01)
(52) U.S. Cl. .......................... 600/391; 600/393; 607/149
(58) Field of Classification Search .................. 607/148, 607/149, 115, 153; 600/372, 386, 393–394
See application file for complete search history.

(56) References Cited

U.S. PATENT DOCUMENTS

| | | | | |
|---|---|---|---|---|
| 4,186,729 A | | 2/1980 | Harrison | 128/1.3 |
| 4,282,886 A | * | 8/1981 | King | 607/130 |
| 4,641,656 A | * | 2/1987 | Smits | 607/5 |
| 5,111,812 A | * | 5/1992 | Swanson et al. | 607/2 |
| 5,114,424 A | | 5/1992 | Hagen et al. | |

FOREIGN PATENT DOCUMENTS

| | | |
|---|---|---|
| CA | 1 219 642 A | 3/1987 |
| DE | 2 018 239 A1 | 11/1970 |
| DE | 42 31 236 A1 | 3/1994 |
| EP | 416 159 A1 | 3/1991 |
| JP | 3-505785 | 12/1991 |
| JP | 10-276995 | 10/1998 |
| JP | 10-325821 | 12/1998 |
| WO | 90/12314 | 10/1990 |
| WO | WO 91/19531 | 12/1991 |

* cited by examiner

*Primary Examiner* — Mark W Bockelman
(74) *Attorney, Agent, or Firm* — Wenderoth, Lind & Ponack, L.L.P.

(57) ABSTRACT

The invention relates to a medical electrode comprising a carrier having a first conductor surface and an outer conductor surface surrounding the first conductor surface wherein the outer conductor surface is free from radial tabs for connection to circuitry so as to remain electrically uncontacted on the carrier.

20 Claims, 3 Drawing Sheets

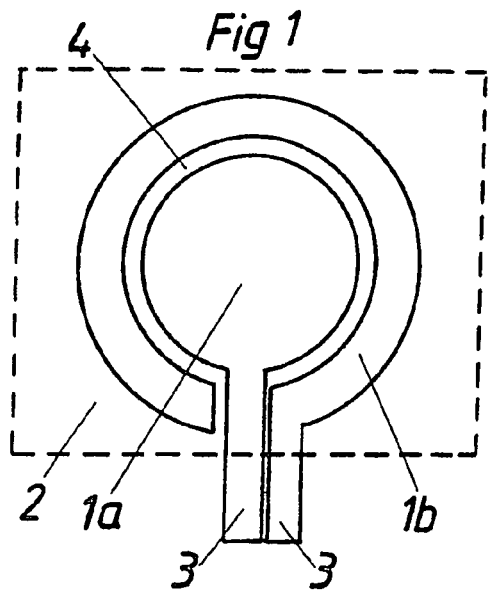
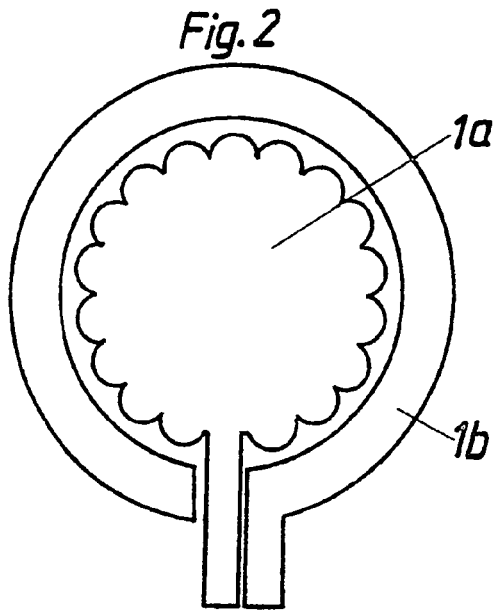
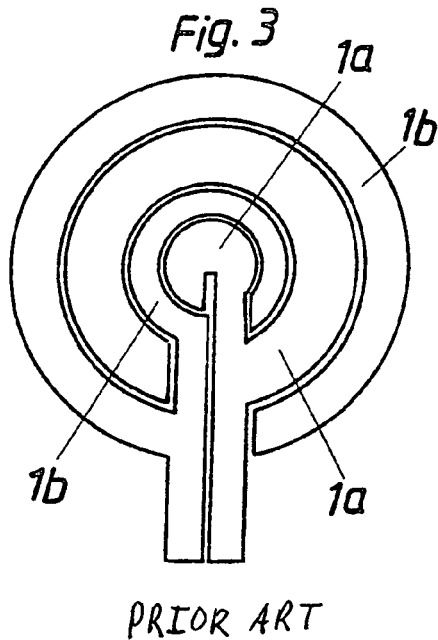
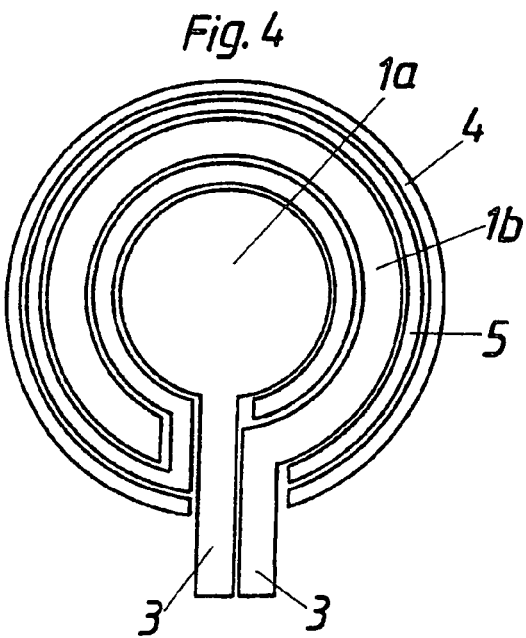

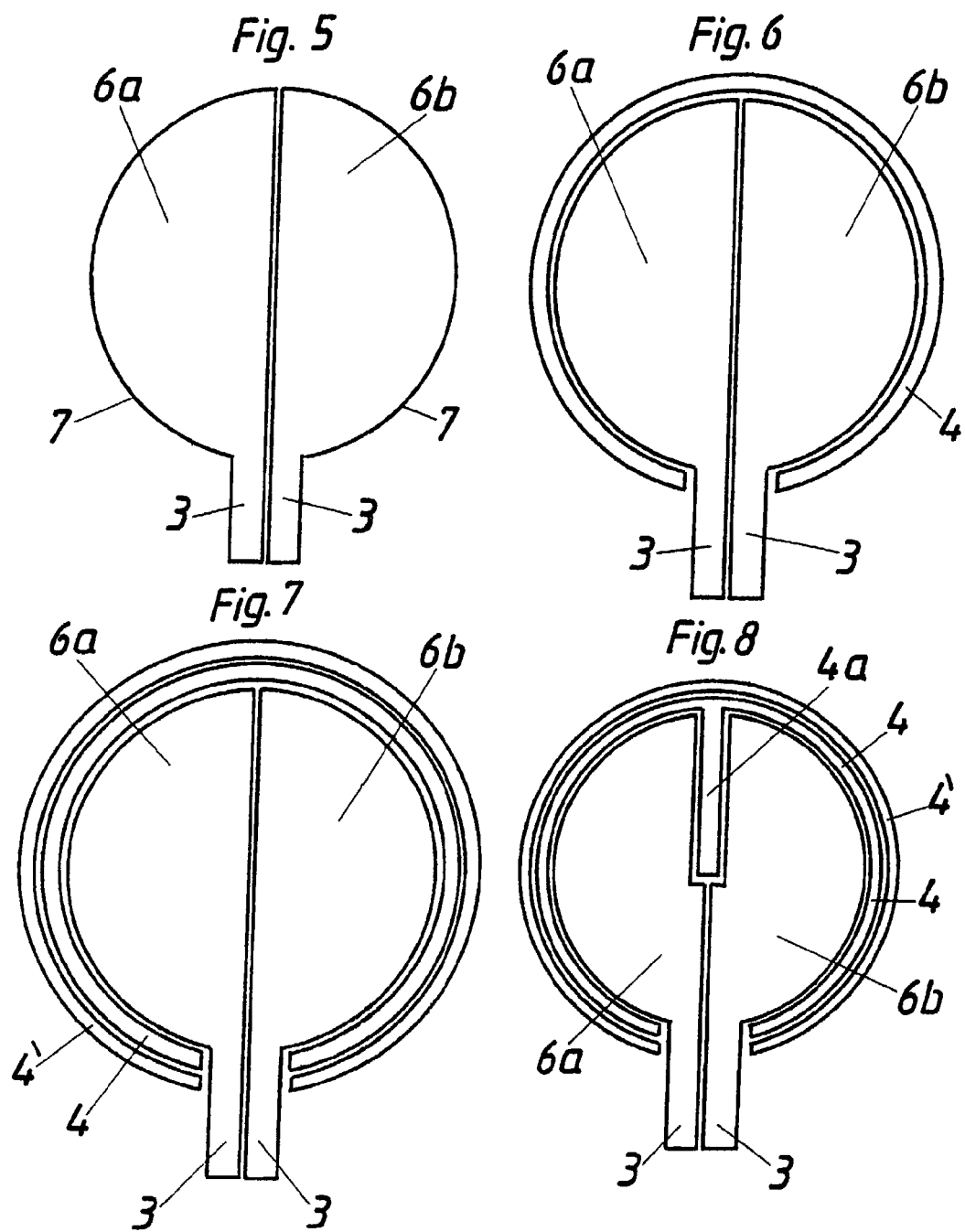

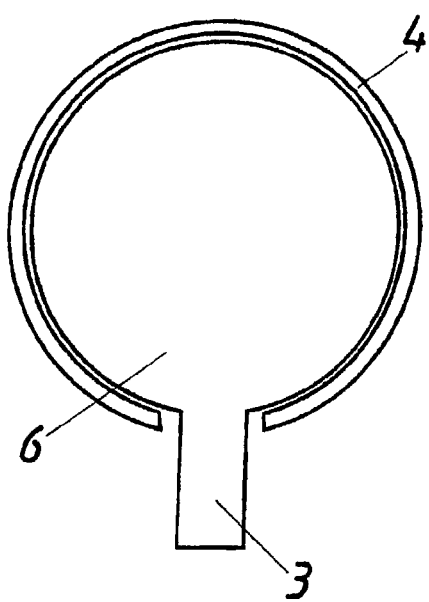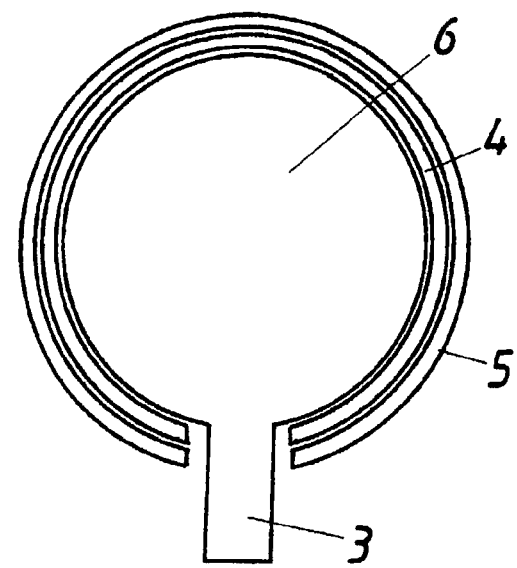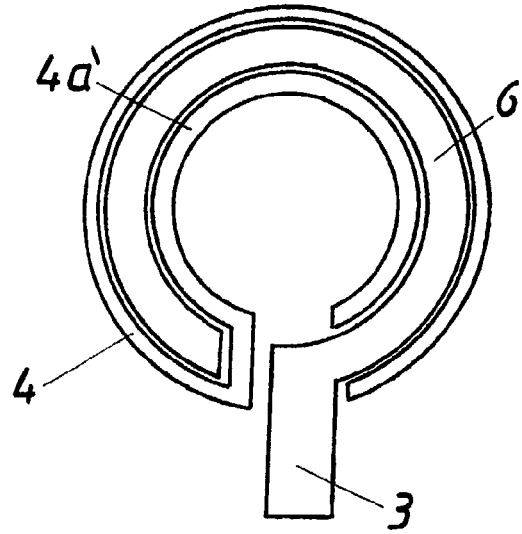

MEDICAL ELECTRODE

BACKGROUND OF THE INVENTION

The invention concerns a medical electrode, in particular for energy transmission, comprising at least one electrically contactable conductor surface preferably provided with a connecting bar or the like.

Such electrodes are applied to the skin of the patient for the most widely varying purposes, for example in order to monitor bioelectrical processes of the body or to introduce into or take from the body currents—which are mostly of relatively high frequency—(for example neutral electrodes, stimulation electrodes and defibrillation electrodes). The structure of those electrodes can be of various different kinds, in general such electrodes have a rearward carrier remote from the skin and comprising a foam material. Provided on the carrier, possibly with the interposition of intermediate layers, are electrically conductive conductor surfaces, for example an aluminum laminate. It is however also possible to provide non-metallic conductor surfaces. In the case of neutral electrodes, they are not directly in contact with the skin, to avoid the occurrence of high local current densities. On the contrary, there is provided an adhesive gel which is electrically conductive for the alternating currents used and which makes the contact with the skin.

In the case of neutral electrodes for taking current from an area of operation it is already known for those electrodes to be equipped with at least two electrically separate conductor surfaces, wherein an electronic evaluation device individually monitors the currents taken from the respective conductor surfaces and gives an alarm in the event of an excessive difference being detected. The purpose of that procedure is to ensure that both conductor surfaces of the neutral electrode afford good electrical contact with the skin in order to exclude local heat-generation phenomena at the skin of the patient. In the case of the known neutral electrode, there are for example two substantially rectangular conductor surfaces which are arranged on a common carrier in mutually juxtaposed relationship with a gap between them. So that this neutral electrode together with the monitoring device connected thereto is operable, the gap must be precisely oriented with respect to the area of operation as otherwise the two conductor surfaces are supplied differently with current.

SUMMARY OF THE INVENTION

In order to improve the apportioning of current, in particular in the case of neutral electrodes for taking off current, and to make such apportioning more uniform, it is provided in accordance with the invention that there is at least one uncontacted conductor surface which is arranged at a spacing and electrically separated from the at least one electrically contactable conductor surface.

The uncontacted conductor surface which is free from connecting bars can for example surround the contacted conductor surface in the form of a circular ring. It is also possible to provide two or more such uncontacted conductor surfaces on a common carrier with the contactable conductor surface or surfaces. It is also possible for the uncontacted conductor surface to extend into the intermediate space between two spaced contacted conductor surfaces.

As already mentioned the aim of those uncontacted conductor surfaces is to improve current apportionment, in particular in the case of neutral electrodes which take off current, and to make it more uniform. Particularly in the case of such neutral electrodes which preferably have two or more electrically contactable conductor surfaces, an additional non-contacted conductor surface ring can result in uniform apportionment of the current to be taken off, to the two electrode portions (conductor surfaces). That therefore overall affords better current density distribution and thus a lower level of thermal loading for the patient.

In order to provide a medical electrode having at least two electrically separated conductor surfaces which permit uniform detection of biopotentials or energy transmission, a preferred embodiment provides that one conductor surface at least partially surrounds another conductor surface, as viewed in plan.

The inner conductor surface is preferably of a round circular configuration and the outer conductor surface surrounds that inner conductor surface in the form of a circular ring. The gap between the two electrically separated conductor surfaces then extends in the form of an annular gap between the inner and the outer conductor surfaces. In accordance with an embodiment, by suitable dimensioning and configuration thereof, it is possible for the surface areas and/or peripheral lengths of the two conductor surfaces which are however different in configuration to be nonetheless substantially equal, in particular in order to provide substantially identical conditions in terms of taking off current in the case of the neutral electrode and to ensure a high level of orientational tolerance.

A substantial advantage of such a preferred electrode configuration provides that, apart from a compact structural shape, it can be stuck on the skin in many different orientations without having to accept a substantial variation in current conductivity (high orientational tolerance, that is to say flexile orientability for example in relation to an area of operation). In that respect it is particularly desirable if the outer conductor surface surrounds the inner over an angular range of over 90°, preferably over 270°. While in the previous neutral electrode in accordance with the state of the art, the gap always had to be oriented accurately with respect to the area of operation, the medical staff can now stick the novel electrode on the skin in virtually any orientation. That makes use considerably easier.

In spite of the fact that the conductor surfaces surround each other with their active regions, it is desirable for the connecting lugs to be taken out laterally in parallel mutually juxtaposed relationship in order to permit simple connection of the multi-pole electrode cable.

A further embodiment of the invention is based on the realisation that higher local current densities can occur at the corners of the conductive regions. In order to avoid that this embodiment of the invention provides that the conductive regions are of a substantially round configuration, preferably being of a round circular configuration. In that way it is possible to avoid the disadvantageous corners and in addition to ensure insensitivity in relation to different orientations when applying the electrode.

BRIEF DESCRIPTION OF THE DRAWING

Further advantages and details of the invention are described in greater detail with reference to the specific description hereinafter.

FIG. 1 diagrammatically shows the arrangement of two electrically separate conductor surfaces in an electrode, wherein the carrier, for example a sticky foam support, is shown in broken line.

FIGS. 2 through 11 further arrangements of conductor surfaces for an electrode, in particular a neutral electrode, wherein carrier materials or possible skin-side, electrically conducting, sticky gels are not shown for the sake of simplicity. In this respect FIGS. 4, 6, 7, 8, 9, 10 and 11 show the uncontacted conductor surface according to the invention.

DETAILED DESCRIPTION OF THE INVENTION

The medical skin electrode shown in FIG. 1 has on a carrier 2 two electrically separate conductor surfaces 1a and 1b provided with connecting bars 3. The outer conductor surface 1b surrounds the inner conductor surface 1a, as can be seen in a plan view as shown in FIG. 1. The inner conductor surface 1a is of a substantially round circular configuration and the outer conductor surface 1b is substantially in the form of a circular ring, with a gap 4 of constant width being arranged therebetween. It is particularly appropriate if the outer conductor surface 1b surrounds the inner conductor surface over an angular range which is as large as possible. That should be at least 90°, preferably over 270°. With such an arrangement it is possible for the electrode to be disposed in virtually any orientation with respect to the area of operation while nonetheless always achieving reliable current take-off which is distributed uniformly to the two surface portions 1a and 1b. When connecting a monitoring apparatus which forms part of the state of the art and which measures the relative currents from the two conductor surfaces 1a and 1b, the situation therefore does not involve an unwanted alarm being triggered off when the electrode is stuck on the skin in virtually any orientation relative to the area of operation. The electrode can thus be applied quickly and in an uncomplicated fashion by the medical specialist staff.

In order to provide conditions which as far as possible are identical for current take-off (in general terms: energy transmission) for the two conductor surfaces 1a and 1b the surface areas of the two surfaces 1a and 1b are here selected to be equal.

In the case of the electrode shown in FIG. 2 the inner conductor surface 1d has a multiply curved outside edge in order to increase the peripheral length thereof so that it substantially corresponds to the peripheral length of the outer hook-shaped or circular ring-shaped conductor surface element 1b.

FIG. 3 shows a 'double hook geometry' in which the conductor surfaces 1a and 1b have hook-shaped projections which are interleaved one into the other in order to achieve uniform current distribution to the two half-electrodes.

The electrode shown in FIG. 4 also has two electrically contacted conductor surfaces 1a and 1b which are interleaved one into the other or which at least partially surround each other. In accordance with the invention this electrode also has two uncontacted rings 4 and 5 which, in contrast to the conductor surfaces 1a and 1b, do not have any connecting elements 3 for an electrode cable. The outer uncontacted ring encloses all inner conductor surfaces while the inner uncontacted ring additionally also extends into the gap between the two contacted conductor surfaces 1a and 1b (the actual active electrode surfaces). The purpose of such uncontacted conductor surfaces or rings 4 and 5 of that kind is to achieve uniform current apportionment. Tests on a patient with neutral electrodes have shown that the use of such uncontacted rings involves a substantially lower level of thermal loading by virtue of improved current density distribution.

Desirably those uncontacted rings and the contacted conductor surfaces 1a and 1b will be arranged on a carrier (not shown in FIG. 4), for example of foam, and, if this is desired, covered with an electrically conducting gel at the skin side. In principle however it is also possible for the uncontacted, electrically conducting rings or the contactable conductor surfaces 1a and 1b to be applied independently of each other to the patient in the form of separate components.

In order to avoid corners being present on rectangular electrode elements, the shape of the conductor surfaces is desirably so selected that they are of a round, preferably round circular external contour (with the exception of the connecting bars 3). Such an embodiment is diagrammatically shown in FIG. 5 where the two conductor surfaces 6a and 6b are of a clearly evident round circular outside contour 7. It will be appreciated that such a simple, round, double-surface double electrode may also be surrounded by an additional uncontacted ring 4 which at least partially encloses the outside contour. In that way once again the rise in temperature of the electrode with the flow of current in the course of medical use can be kept particularly low and uniform. In the embodiment illustrated in FIG. 7 there is also a further ring 4' disposed outside the uncontacted ring 4, that is to say a total of two uncontacted rings which result in the current flow in use being rendered still more uniform. It is also possible for the uncontacted conductor surface 4 to have an extension 4a which extends into the region between the two electrically contacted conductor surfaces.

The idea of a medical electrode with an electrically uncontacted, preferably annular conductor surface 4 or 5 respectively can also be embodied in electrodes with only one electrically contacted conductor surface 6, as is shown in FIGS. 9, 10 and 11. In regard to FIG. 11 it should also be mentioned that here the current-carrying contacted electrode 6 is of a substantially hook-shaped configuration, wherein the contact-less outer ring 4 extends inwardly with an extension 4'a and thus also covers the inside of the hook electrode.

The invention claimed is:

1. A medical neutral electrode, comprising:
   a carrier having a skin side for attaching said neutral electrode to the skin of a patient;
   at least one electrically contactable conductor surface arranged on said carrier, said at least one electrically contactable conductor surface having a connecting element for connection to circuitry;
   at least one current-equalizing conductor surface that is arranged on said carrier (a) at a spacing from said at least one electrically contactable conductor surface, (b) so as to be electrically separated from said at least one electrically contactable conductor surface and (c) so as to surround said at least one electrically contactable conductor surface on said carrier;
   wherein said at least one current-equalizing conductor surface is free from radial tabs for connection to circuitry in order to remain electrically uncontacted on said carrier; and
   an adhesive and electrically conductive gel on the skin side of said carrier.

2. The medical electrode as set forth in claim 1 wherein said connecting element is a tab.

3. The medical electrode as set forth in claim 1, wherein said at least one current-equalizing conductor surface extends along said at least one electrically contactable conductor surface.

4. The medical electrode as set forth in claim 1, wherein said at least one current-equalizing conductor surface surrounds a plurality of current-equalizing conductor surfaces on said carrier.

5. The medical electrode as set forth in claim 1, wherein said at least one current-equalizing conductor surface is shaped as a circular ring.

6. The medical electrode as set forth in claim 1, wherein said at least one current-equalizing conductor surface comprises a conductor surface that extends into an intermediate space between two spaced electrically contactable conductor surfaces arranged on said carrier or into a recess configuration in a conductor surface.

7. The medical electrode as set forth in claim 1, wherein said at least one current-equalizing conductor surface comprises two current-equalizing conductor surfaces that are curved parallel.

8. The medical electrode of claim 1, wherein said at least one electrically contactable conductor surface comprises at least two electrically separated contactable conductor surfaces arranged on said carrier, wherein one of said electrically contactable conductor surfaces at least partially surrounds another of said conductor surfaces.

9. The medical electrode as set forth in claim 8, wherein an inner one of said at least two electrically separated contactable conductor surfaces is surrounded by an outer conductor surface of said at least two electrically separated contactable conductor surfaces, said outer conductor surface extending around said inner said conductor surface with a constant gap spacing relative to an outer edge thereof.

10. The medical electrode as set forth in claim 8, wherein an inner conductor surface of said at least two electrically separated contactable conductor surfaces is of a substantially round circular configuration and is surrounded by an outer conductor surface of said at least two electrically separated contactable conductor surfaces, said outer conductor surface being in the form of a circular ring.

11. The medical electrode as set forth in claim 8, wherein an outer conductor surface of said at least two electrically separated contactable conductor surfaces surrounds an inner conductor surface of said at least two electrically separated contactable conductor surfaces over an angular range of more than 270°.

12. The medical electrode as set forth in claim 8, wherein at least one inner conductor surface of said at least two electrically separated contactable conductor surfaces and an outer conductor surface of said at least two electrically separated contactable conductor surfaces surrounding said inner conductor surface have respective projecting contacting elements for electrode cables, wherein said connecting elements are arranged laterally, one beside the other, and parallel to each other.

13. The medical electrode of claim 8, wherein said at least two electrically separated contactable conductor surfaces comprises two electrically contactable conductor surfaces that are in different radial positions and that have surface areas and peripheral lengths thereof that are substantially equal.

14. The medical electrode of claim 8, wherein said at least two electrically separated contactable conductor surfaces comprise at least one conductor surface of a hook-shaped configuration, said hook-shaped configuration surrounding another of said at least two electrically separated contactable conductor surfaces.

15. The medical electrode of claim 8, wherein each of said at least two electrically separated contactable conductor surfaces comprise hook-shaped projections that are interleaved one into the other.

16. The medical electrode as set forth in claim 1, wherein an outside contour of said at least one electrically contactable conductor surface is round.

17. A method of equalizing the current in a medical neutral electrode, comprising the steps of:
providing a medical neutral electrode comprising a carrier having a skin side with an adhesive and electrically conductive gel thereon and attaching said neutral electrode to the skin of a patient, at least one electrically contactable conductor surface arranged on the carrier, the at least one electrically contactable conductor surface having a connecting element, at least one current-equalizing connector surface that is arranged on the carrier (a) at a spacing from the at least one electrically contactable conductor surface, (b) so as to be electrically separated from the at least one electrically contactable conductor surface and (c) so as to surround the at least one electrically contactable conductor surface on the carrier, wherein the at least one current-equalizing conductor surface is free from radial tabs for connection to circuitry in order to remain electrically uncontacted on the carrier;
connecting circuitry that delivers to or monitors energy from the at least one electrically contactable conductor surface;
delivering or receiving an energy transmission from the circuitry to the at least one electrically contactable conductor surface while leaving the at least one current-equalizing conductor surface on the carrier electrically unconnected to circuitry and equalizing the distribution of the current with the at least one current-equalizing conductor surface on the carrier.

18. The method of according to claim 17, further comprising providing the medical neutral electrode so that the at least one current-equalizing conductor surface extends along the at least one electrically contactable conductor surface.

19. The method according to claim 17, further comprising providing the medical neutral electrode so that the at least one current-equalizing conductor surface surrounds a plurality of electrically contactable conductor surfaces.

20. A medical system comprising:
circuitry selected from the group consisting of circuitry that monitors biopotentials and circuitry that provides electrical energy to a patient; and
a medical neutral electrode comprising a carrier having a skin side with an adhesive and electrically conductive gel thereon for attaching said neutral electrode to the skin of a patient, at least one electrically contactable conductor surface arranged on the carrier, the at least one electrically contactable conductor surface having a connecting element for connection to circuitry, at least one current-equalizing conductor surface that is arranged on the carrier (a) at a spacing from the at least one electrically contactable conductor surface, (b) so as to be electrically separated from the at least one electrically contactable conductor surface and (c) so as to surround the at least one electrically contactable conductor surface on the carrier, wherein the at least one current-equalizing conductor surface is free from radial tabs for connection to circuitry in order to remain electrically uncontacted on the carrier, and wherein the at least one current-equalizing conductor surface is spaced from the at least one electrically contactable conductor surface so as to provide improved current density distribution.

* * * * *